United States Patent
Luyken et al.

(10) Patent No.: US 9,822,067 B2
(45) Date of Patent: Nov. 21, 2017

(54) METHOD FOR PURIFYING ADIPODINITRILE (ADN)

(71) Applicant: BASF SE, Ludwigshafen (DE)

(72) Inventors: Hermann Luyken, Ludwigshafen (DE); Peter Pfab, Ludwigshafen (DE); Tim Jungkamp, Kapellen (BE)

(73) Assignee: BASF SE (Ellwanger & Baier Patentanwälte), Ludwigshafen (DE)

( * ) Notice: Subject to any disclaimer, the term of this patent is extended or adjusted under 35 U.S.C. 154(b) by 0 days.

(21) Appl. No.: 15/116,541

(22) PCT Filed: Feb. 3, 2015

(86) PCT No.: PCT/EP2015/052127
§ 371 (c)(1),
(2) Date: Aug. 4, 2016

(87) PCT Pub. No.: WO2015/117933
PCT Pub. Date: Aug. 13, 2015

(65) Prior Publication Data
US 2016/0376227 A1    Dec. 29, 2016

(30) Foreign Application Priority Data
Feb. 7, 2014 (EP) .................................... 14154300

(51) Int. Cl.
C07C 253/34    (2006.01)
(52) U.S. Cl.
CPC .................................. *C07C 253/34* (2013.01)
(58) Field of Classification Search
CPC ................................................... C07C 253/34
See application file for complete search history.

(56) References Cited

U.S. PATENT DOCUMENTS

| | | | |
|---|---|---|---|
| 6,359,178 B1 * | 3/2002 | Fischer ................ | C07C 209/48 564/492 |
| 7,501,045 B2 | 3/2009 | Gerber et al. | |
| 7,528,275 B2 | 5/2009 | Bartsch et al. | |
| 7,781,608 B2 * | 8/2010 | Scheidel .............. | C07C 253/10 558/335 |
| 7,935,229 B2 | 5/2011 | Deckert et al. | |
| 9,040,733 B2 * | 5/2015 | Moerbe ................ | C07C 253/10 558/308 |
| 2013/0289299 A1 | 10/2013 | Fischer et al. | |
| 2016/0009633 A1 | 1/2016 | Luyken et al. | |

FOREIGN PATENT DOCUMENTS

| | | |
|---|---|---|
| CN | 202942671 U | 5/2013 |
| DE | 1 268 611 B | 5/1968 |
| EP | 1 817 108 A2 | 8/2007 |
| WO | WO-2005/019160 A1 | 3/2005 |
| WO | WO-2005/073167 A1 | 8/2005 |
| WO | WO-2006/042675 A2 | 4/2006 |
| WO | WO-2014/131674 A2 | 9/2014 |

OTHER PUBLICATIONS

International Search Report for PCT/EP2015/052127 dated Apr. 24, 2015.
Apre, Hans-Jürgen, "Industrielle Organische Chemie", 6$^{th}$ Edition, Wiley VCH-Verlag, 2007, pp. 272-273.
Marion, P., et al., "Hydrogenation of Dinitriles into Diamines-Influence of the Nature of Dinitrile on Activity and Selectivity of the Reaction" in "Heterogeneous Catalysis and Fine Chemicals III", Guisnet, M., et al., Eds., Elsevier, 1993, pp. 291-297.
Yen, Y.-C., et al., "Hexamethylenediamine from Butadiene via Hydrocyanation to Adiponitrile" in Process Economics Program Report No. 54, Suppl. B, Nylon 6.6 Supp. B, 1987, pp. 201-214 and 571-575.
International Preliminary Report on Patentability and English Translation thereof in PCT/EP2015/052127 Dated Aug. 9, 2016.

* cited by examiner

*Primary Examiner* — Golam M M Shameem
(74) *Attorney, Agent, or Firm* — Drinker Biddle & Reath LLP

(57) ABSTRACT

The present invention relates to a process for purifying adiponitrile (ADN), wherein crude ADN is introduced into a rectification apparatus (R1). The rectification apparatus (R1) comprises a first side draw and preferably also a second side draw, the first side draw being disposed below the crude ADN introduction point and the optional second side draw being disposed above the crude ADN introduction point. The first side draw is used to draw off a gaseous stream comprising ADN while the optional second side draw is used to draw off undesired by-products such as 1-amino-2-cyano-cyclopentene (ACCP) which are often generated in ADN production and consequently may be present in the crude ADN. The gaseous stream from the first side draw of (R1) is introduced into a second rectification apparatus (R2). (R2) is used to separate off ADN from remaining high boilers and any other by-products present, pure ADN being drawn off from (D2) as overhead product. It is preferable when the process according to the invention employs crude ADN from a reaction of butadiene with hydrocyanic acid (HCN).

20 Claims, 3 Drawing Sheets

METHOD FOR PURIFYING ADIPODINITRILE (ADN)

RELATED APPLICATIONS

Figure 1:
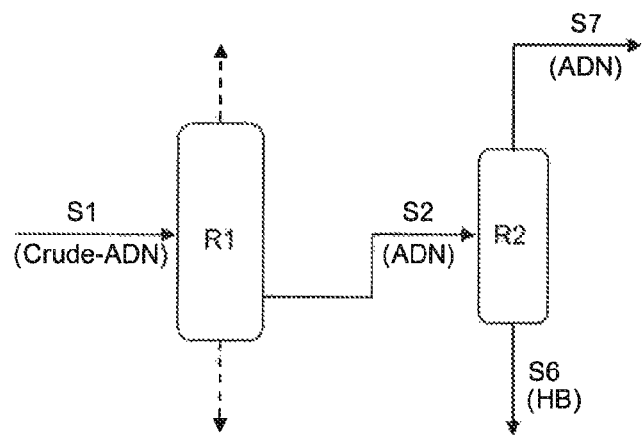

This application is a national stage application (under 35 U.S.C. §371) of PCT/EP2015/052127, filed Feb. 3, 2015, which claims benefit of European Application No. 14154300.9, filed Feb. 7, 2014.

The present invention relates to a process for purifying adiponitrile (ADN), wherein crude ADN is introduced into a rectification apparatus (R1). The rectification apparatus (R1) comprises a first side draw and preferably also a second side draw, the first side draw being disposed below the crude ADN introduction point and the optional second side draw being disposed above the crude ADN introduction point. The first side draw is used to draw off a gaseous stream comprising ADN while the optional second side draw is used to draw off undesired by-products such as 1-amino-2-cyanocyclopentene (ACCP) which are often generated in ADN production and consequently may be present in the crude ADN. The gaseous stream from the first side draw of (R1) is introduced into a second rectification apparatus (R2). (R2) is used to separate off ADN from remaining high boilers and any other by-products present, pure ADN being drawn off from (D2) as overhead product. It is preferable when the process according to the invention employs crude ADN from a reaction of butadiene with hydrocyanic acid (HCN).

Adiponitrile can, in principle, be produced on a large industrial scale by 3 different processes. Specifically, such production is carried out by (i) reaction of adipic acid with ammonia, (ii) by dimerization of acrylonitrile or (iii) by hydrocyanation of butadiene with hydrocyanic acid.

The third and preferred process alternative comprises producing adiponitrile from butadiene and hydrocyanic acid in a multistage process. The first step comprises reacting butadiene with hydrocyanic acid in the presence of nickel(0) phosphorus ligand complexes to afford mixtures comprising predominantly 3-pentenenitrile and 2-methyl-3-butenenitrile. 3-Pentenenitrile and 2-methyl-3-butenenitrile are separated by distillation. 2-Methyl-3-butenenitrile is isomerized to afford 3-pentenenitrile. The second step comprises hydrocyanation of 3-pentenenitrile with hydrocyanic acid in the presence of nickel(0) phosphorus ligand complexes and, in addition, a Lewis acid to afford adiponitrile (see also Hans-Jürgen Arpe, lndustrielle Organische Chemie, 6th edition (2007), Wiley VCH-Verlag, pages 272 to 273 or WO 2006/042675). This initially generates adiponitrile in the form of so-called crude ADN.

WO 2005/073167 shows that the nickel(0) phosphorus ligand complexes employed as catalyst in the production of ADN by hydrocyanation of 1,3-butadiene in a two-stage process comprise monodentate and bidentate phosphorus ligands from the group of phosphites, phosphinites and phosphonites.

In industry, this crude ADN which may also be produced by a process other than the butadiene route is often subjected directly to further processing comprising purification by distillation (to obtain pure ADN) and subsequent hydrogenation in the presence of a hydrogenation catalyst, for example Raney nickel, to afford hexamethylenediamine (HMD). The reaction thereof with adipic acid is a route, via what is known as AH salt, to polyamide 6,6 by thermal polycondensation.

Crude adiponitrile comprises not only the main product adiponitrile but also a range of by-products, the type and/or amount of the by-products in question depending on the chosen ADN production process. By-products generated include, in particular, branched dinitriles such as 2-methylglutaronitrile (2-MGN), 2-ethylsuccinonitrile (2-ESN) and 1-amino-2-cyanocyclopentene (ACCP). The branched dinitriles are formed, for example, in the hydrocyanation of 3-pentenenitrile. However, 1-amino-2-cyanocyclopentene is also formed by intramolecular cyclization of adiponitrile, particularly at relatively high temperatures. 1-Amino-2-cyanocyclopentene (ACCP, also known as ICCP) is a tautomer of 1-imino-2-cyanocyclopentane (CCPI or CPI) (P. Marion et al., Heterogeneous Catalysis and Fine Chemicals III (1993), page 293):

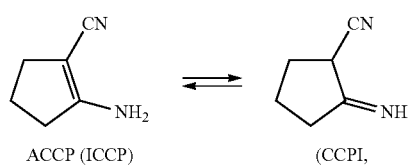 [SMILES: N#CC1=C(N)CCC1 ; N#CC1CCCC1=N]

In the ADN hydrogenation, secondary components not separated off by distillation (dinitriles and/or amononitriles) are hydrogenated to give diamines which, in the polycondensation to afford polyamides, lead to premature chain termination and thus to yellowing of said polyamides (see also DE-A 1 268 611, column 1, lines 19 bis 27). The secondary components should thus be separated off as completely as possible before the ADN hydrogenation. It is disclosed in DE-A 1 268 611 for example, that in the case of 1-amino-2-cyanocyclopentene the amount formed may be reduced by lowering the bottom temperatures in the ADN distillation.

DE-A 1 268 611 further discloses a process for purifying adiponitrile by distillation using three columns. ADN is drawn off from the bottom of the second distillation column. The third column is required to recover the large amounts of ADN that are drawn off overhead with the low boilers in the distillation in the second column. The crude ADN employed in DE-A 1 268 611 comes from the reaction of adipic acid with ammonia.

Process Economics Program Report No. 54 B, Nylon 6.6 Supp. B, September 1987, pages 201 to 214 in connection with pages 571 to 575 (FIG. 10.1), discloses converting crude ADN produced by hydrocyanation into pure ADN by distillation using three columns. Starting from crude adiponitrile produced by the butadiene route, this process comprises separating off unconverted 3-pentenenitrile as overhead product (stream 42) in a first column (C-303, ADN column), The bottoms from the first column (stream 41) are supplied to a second column (C-401, isomer column) in which a mixture of 2-methylglutaronitrile and 2-ethylsuccinonitrile is separated off as overhead product. The bottoms from the second column (stream 53) are supplied to a third column (C-402, purification column) from which adiponitrile is drawn off overhead. The overhead temperature of the third column is 369° F. (187° C.) at 27 mmHg (36 mbar), the bottom temperature is 400° F. (204° C.). The bottoms from the third column consist of high boilers which are discharged and, where necessary, disposed of. One disadvantage of the process described is that the production of pure adiponitrile by distillation requires three distillation columns. A further disadvantage is that the bottom temperature of the third column is in excess of 200° C. with the result that appreciable amounts of adiponitrile are converted into 1-amino-2-cyanocyclopentene and, after hydrogenation, are reacted to give 2-aminomethylcyclopentylamine which is difficult to separate off from hexamethylenediamine.

WO 2005/019160 A1 discloses supplying crude adiponitrile (stream 13), produced by hydrocyanation of butadiene and 3-pentenenitrile with hydrocyanic acid, to a column 14. The overhead product drawn off from the column (stream 45) is composed overwhelmingly of pentenenitriles, the bottoms (stream 17) being composed of high boilers. A side draw of the column 14 (stream 19) is used to draw off dinitrile mixtures comprising adiponitrile, 2-methylglutaronitrile and 2-ethylsuccinonitrile. Isolating pure ADN from this dinitrile mixture in turn requires further laborious separation steps, the execution of which is, however, not specifically disclosed in WO 2005/019160 A1.

A particular disadvantage of the process described in WO 2005/019160 A1 is that, at 285° C./1013 mbar, the boiling point of 1-amino-2-cyanocyclopentene formed from adiponitrile (bp=303° C./1013 mbar) lies between the boiling points of ADN and its branched isomers 2-MGN (bp=274° C./1013 mbar) and 2-ESN (bp=265° C./1013 mbar). Accordingly, the mixture drawn off from side draw 19 in the process according to WO 2005/019160 A1 comprises not only ADN but also considerable amounts of 2-MGN, 2-ESN and ACCP. It is, however, necessary to separate off from this mixture the target product adiponitrile in pure form. This accordingly requires further distillation columns.

The present invention has for its object the provision of a novel process for purifying adiponitrile (ADN) starting from crude ADN.

The object is achieved in accordance with the invention by a process for purifying adiponitrile (ADN) comprising the following steps a) to c):

a) introducing a stream (S1) comprising crude adiponitrile (crude ADN) into a rectification apparatus (R1), b) separating off a gaseous stream (S2) via a first side draw of (R1), wherein the first side draw of (R1) is disposed below the introduction point for introducing stream (S1) into (R1) and wherein gaseous stream (S2) comprises ADN, and c) introducing gaseous stream (S2) into a second rectification apparatus (R2), wherein an ADN stream (S7) depleted in high-boilers (HB) is drawn off from (R2) as overhead product and a liquid stream (S6) enriched in high boilers (HB) is drawn off from (R2) as bottoms.

The process according to the invention makes it possible to produce ADN, in particular high-purity ADN, in an advantageous fashion. The process according to the invention may be used to purify any crude ADN, irrespective of its specific production process. The process according to the invention overcomes, in particular, the disadvantages described hereinabove in connection with the purification of crude ADN produced by the butadiene route.

A further advantage of the process according to the invention is that it is very flexible. The process according to the invention can be optimized further depending on the crude ADN employed. For example, when the crude ADN employed comprises ACCP, the process according to the invention is advantageously carried out such that the rectification apparatus (R1) comprises a second side draw. This second side draw of (R1) disposed above the introduction point for introducing stream (S1) into (R1) can be used to separate off a stream (S3) from (R1), said stream (S3) comprising 1-amino-2-cyanocyclopentene (ACCP) and any further undesired by-products present such as 2-MGN and/or 2-ESN in particular.

The fact that high boilers, preferably volatile high boilers, generally present in the crude ADN may be separated off from the ADN in simple fashion may also be regarded as a further advantage of the process according to the invention. These preferably volatile high boilers are initially drawn off from the rectification apparatus (R1) via the gaseous side draw (from the stripping section, i.e. below the introduction point for stream (S1)) together with (the majority of) the ADN. These volatile high boilers may be efficaciously depleted/separated off in only a single further column (rectification apparatus (R2)) and pure ADN may therefore be obtained from (R2) as overhead product. The rectification apparatus (R2) may be operated without an additional evaporator which is likewise an advantage of the process according to the invention.

However, the process according to the invention has the general advantage that it economizes on apparatuses, particularly rectification and/or distillation columns. The process according to the invention allows the vast majority of disruptive by-products normally generated, particularly ACCP, 2-MGN and/or 2-ESN, to be separated off as one fraction and optionally disposed of together. Said process can also avoid the problem of solid formation addressed in DE-A 1 268 611 because ACCP for example, which is solid at room temperature, is discharged from the process with the other (generally liquid) by-products as a component of stream (S3) to prevent the occurrence of side draw blockages. Suitable adjustment of process parameters, particularly of pressure and temperature, allows the process according to the invention to be operated such that, irrespective of the further components of stream (S3), blockages due to potential ACCP precipitation are avoided. However, the process according to the invention is preferably carried out such that stream (S3), the second side draw from rectification apparatus (R1), comprises not only ACCP but also further by-products, particularly branched dinitriles such as 2-ESN and/or 2-MGN, since ACCP is readily soluble in the branched dinitriles.

A further advantage of the process according to the invention is that the distillative purification of crude ADN affords pure ADN, i.e. ADN having a degree of purity of at least 99.0%, more particularly high purity ADN, while requiring, in principle, only two rectification apparatuses (D1 and D2). High purity ADN is to be understood as meaning a stream having an ADN content greater than 99.0%, more particularly greater than 99.5% In addition, drawing off ADN from rectification device (R1) in gaseous form means that the second rectification apparatus (R2) eschews an evaporator.

It is moreover advantageous that very little, if any, ADN is lost in the process according to the invention on account of appropriate recycling. Virtually all of the ADN present in the crude ADN can be purified to afford pure ADN.

The process according to the invention for purifying ADN is more particularly defined hereinbelow.

Step a) of the process according to the invention comprises introducing a stream (S1) comprising crude adiponitrile (crude ADN) into a rectification apparatus (R1). The stream (S1) may be vaporous or liquid.

Crude ADN as such is known to those skilled in the art and comprises ADN (as such). As already described hereinabove, the crude ADN may comprise, as a function of specific crude ADN production processes, numerous further components, such as by-products, reactants or other compounds. Stream (S1) of the process according to the invention may comprise any proportion of ADN and any proportions of all other components. The proportion of ADN in stream (S1) is preferably greater than 30 wt %, more preferably greater than 40 wt %, most preferably greater than 50 wt %.

Examples of further components (in addition to ADN as such) that may be present in crude ADN of stream (S1) and, as the case may be, in other streams of the process according to the invention such as, for example, stream (S8) further defined hereinbelow include, for example, the following:

The hydrocyanation of 3-pentenenitrile with hydrocyanic acid in the presence of nickel(0) phosphorus ligand complexes and Lewis acids, for example zinc chloride, to afford adiponitrile forms complex product mixtures. These comprise the target product adiponitrile and also the branched dinitriles 2-methylglutaronitrile (2-MGN) and 2-ethylsuccinonitrile (2-ESN). They further comprise pentenenitriles, unconverted or formed by isomerization, such as trans-3-pentenenitrile, cis-3-pentenenitrile, 4-pentenenitrile, cis-2-pentenenitrile, trans-2-pentenenitrile (the boiling range thereof being from 127° C./1013 mbar to 146° C./1013 mbar), 1-amino-2-cyanocyclopentene formed from adiponitrile, nickel(0) phosphorus ligand complexes, free ligands of the nickel(0) complexes and high boilers (HB).

In the context of the present invention, high boilers are to be understood as meaning compounds having a higher boiling point than adiponitrile. Depending on their type, these may have a measurable vapor pressure (e.g. dimers) or no vapor pressure (e.g. salts).

The high boilers may in turn be distinguished as volatile high boilers or non-volatile high boilers. As is apparent from the descriptions which follow, the non-volatile high boilers (the majority or preferably the entirety thereof) are preferably already separated off from the crude ADN before said crude ADN is introduced into rectification apparatus (R1). Volatile high boilers, by contrast, are preferably separated off from ADN (entirely or at least largely) using rectification apparatus (R2). Gaseous stream (S2) which is separated off from (R1) via the first side draw thereof thus comprises these (volatile) high boilers and ADN.

Volatile high boilers may be monodentate or bidentate phosporous ligands or dimeric pentenenitriles or dinitriles for example, non-volatile high boilers may be zinc chloride or iron chloride for example.

The nickel(0) phosphorus ligand complexes and the corresponding free phosphorus ligand complexes are preferably separated off from the product mixtures by extraction with hydrocarbons (as described in EP 1 817 108 B1 for example).

Step b) of the process according to the invention comprises separating off a gaseous stream (S2) via a first side draw of (R1), wherein the first side draw of (R1) is disposed below the introduction point for introducing stream (S1) into (R1) and wherein gaseous stream (S2) comprises ADN. It is preferable when the gaseous stream (S2) is drawn off via the first side draw from the bottom of (R1).

The proportion of ADN in the gaseous stream (S2) is normally greater than 80 wt %, particularly preferably greater than 90 wt %, most preferably greater than 95 wt %. As is explained hereinbelow, gaseous stream (S2) may comprise not only ADN but also further components, such as high boilers, more particularly volatile high boilers.

Step c) of the process according to the invention requires introducing gaseous stream (S2) into a second rectification apparatus (R2), wherein an ADN stream (S7) depleted in high boilers (HB) is drawn off from (R2) as overhead product and a liquid stream (36) enriched in high boilers (HB) is drawn off from (R2) as bottoms.

In other words, the second rectification apparatus (R2) makes it possible to obtain the target product ADN in purified form from the process according to the invention. If the bottoms from (R2) still comprise ADN, this may, for example, be returned to rectification apparatus (R1) as described further hereinbelow.

The bottom temperature of rectification apparatus (R1) is normally from 120° C. to 240° C., preferably from 150° C. to 220° C., more preferably from 160° C. to 190° C. The overhead pressure of (R1) is normally from 3 to 250 mbar, preferably from 10 to 150 mbar, more preferably from 15 to 50 mbar.

The bottom temperature of rectification apparatus (R2) is normally from 120° C. to 240° C., preferably from 150° C. to 220° C., more preferably from 160° C. to 190° C.

The overhead pressure of rectification apparatus (R2) is normally from 3 to 250 mbar, preferably from 10 to 150 mbar, more preferably from 15 to 50 mbar.

The inventive rectification apparatuses (R1) and/or (R2) may take any suitable form known to those skilled in the art. Suitable apparatuses are as described, for example, in: Kirk-Othmer, Encyclopedia of Chemical Technology, 4th edition, volume 8. John Wiley and Sons, New York 1996, pages 334 to 348, such as sieve tray columns, bubble-cap tray columns, columns with structured packing and columns with random packing.

The rectification apparatuses (R1) and/or (R2) preferably comprise internals to enhance separation performance. The internals may take the form, for example, of a structured packing, for example a sheet metal packing such as Mellapak 250 Y or Montz Pak, Type B1-250. It is also possible to use a packing having a reduced or increased specific surface area, a fabric packing or a packing having a different geometry than Mellapak 252 Y. The advantage of using these internals is the low pressure drop and the low specific liquid holdup compared to valve trays for example. The internals may be disposed in one or more beds.

The number of theoretical plates in rectification apparatus (R1) is normally from 15 to 50, preferably from 20 to 40, more preferably from 25 to 35 and/or the number of theoretical plates in rectification apparatus (R2) is normally from 3 to 20, preferably from 5 to 17, more preferably from 8 to 12.

A basic version of the process according to the invention and comprising steps a) to c) is illustrated in FIG. 1. For clarity, in addition to the streams (S1), (S2), (S6) and (S7), FIG. 1 also shows, in brackets, the components essential to the process according to the invention/the separation. As detailed hereinabove or hereinbelow, the respective streams may further comprise additional components. The two dashed arrows shown at the top and bottom of (R1) denote additional streams which are preferably likewise drawn off from the rectification apparatus (R1) in the context of the present invention. These streams are more particularly described in the text which follows in connection with process steps e) and f) and, for example, FIG. 3.

It is further preferable in the context of the process according to the invention when the crude adiponitrile (crude ADN) in stream (S1) comprises adiponitrile (ADN), pentenenitriles (PNs), high boilers (HB), 1-amino-2-cyano-cyclopentene (ACCP), 2-methylglutaroni rile (2-MGN) and 2-ethylsuccinonitrile (2-ESN).

It is further preferable in the context of the process according to the invention when gaseous stream (S2) is introduced into the bottom of (R2) and pure ADN is drawn off from (R2) as overhead product.

It is further preferable in accordance with the invention when the ADN drawn off from (R2) as overhead product has a purity of at least 99.0%, preferably at least 99.5%, more preferably at least 99.8% and/or the total amount of PNs, ACCP, 2-MGN and 2-ESN in the ADN drawn off from (D2) as overhead product is no more than 500 ppm, more preferably no more than 200 ppm, more particularly no more than 100 ppm.

It is further preferable in the process according to the invention when stream (S6) comprising high boilers (HB) and ADN is drawn off from the bottom of (R2) and some or all of said stream is returned to the bottom of rectification apparatus (R1).

It is further preferable in accordance with the invention when rectification apparatuses (R1) and (R2) are each independently columns with structured packing. It is likewise preferable when rectification apparatus (R2) does not have an evaporator.

One preferred embodiment of the present invention comprises carrying out not only steps a) to c) described hereinabove but also at least one of steps d), e) and f) described hereinbelow. In principle, the process according to the invention according to steps a) to c) can be combined with any individual step d), e) and/or f). However, it is particularly preferable when the process according to the invention comprises carrying out a combination of steps a) to f). The individual steps d), e) and f) are defined as follows:

Step d) comprises separating off a stream (S3) via a second side draw of rectification apparatus (R1), wherein the second side draw of (R1) is disposed above the introduction point for introducing stream (S1) into (R1) and wherein stream (S3) comprises 1-amino-2-cyanocyclopentene (ACCP).

Step e) comprises separating off a stream (S5) as overhead product from rectification apparatus (R1), wherein stream (S5) comprises pentenenitriles (PNs), particularly 3-pentenenitrile (3-PN).

Step f) comprises separating off a stream (S4) from the bottom of rectification apparatus (R1), wherein stream (S4) comprises high boilers (HB).

It is particularly preferable in the context of this embodiment of the present invention when
i) stream (S4) comprises high boilers and ADN and is liquid, and/or
ii) stream (S3) comprises ACCP, 2-MGN and 2-ESN and is liquid, and/or
iii) the gaseous stream (S2) comprises ADN, high boilers and no more than 500 ppm of PNs. ACCP, 2-MGN and/or 2-ESN, preference being given to a total amount of PNs, ACCP, 2-MGN and 2-ESN in (S2) of no more than 500 ppm, more preferably no more than 200 ppm, more particularly no more than 100 ppm.

Figure 3:
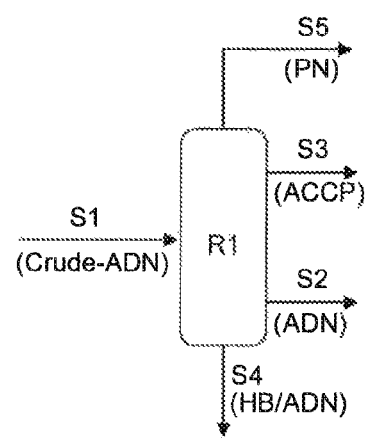
Figure 4:
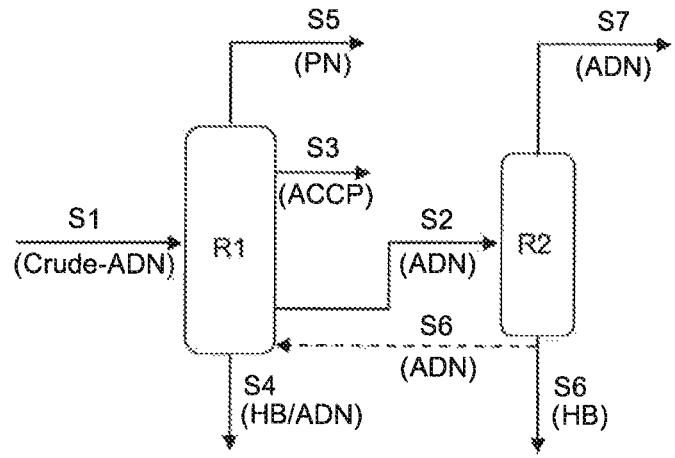

The preferred elaborations/embodiments of the present invention described hereinabove are illustrated in FIGS. 3 and 4. In these figures and all other figures of the present invention the abbreviations, arrows and other symbols have a meaning analogous to that set out in connection with FIG. 1 unless otherwise stated. FIG. 3 illustrates a preferred elaboration of rectification apparatus (R1) that also accounts for the three optional steps d), e) and f). FIG. 4 in turn shows how the preferred embodiment of the rectification apparatus (R1) is integrated into the overall process. The dashed arrow is intended to show that it is also optionally conceivable to recycle any ADN present in stream (S6) into the rectification apparatus (R1). If stream (S6) from (R2) is not returned to (R1), the high boilers separated off via stream (S6), preferably volatile high boilers, are preferably separated off completely from the process according to the invention. The components of stream S6 may, for example, be disposed of and/or put to an alternative use. If stream (S6) comprises appreciable amounts of ADN, it is preferable in accordance with the invention to return at least some and preferably all of stream (S6) from (R2) to (R1).

Figure 2:
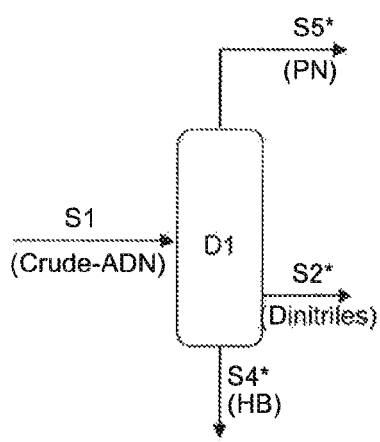

To illustrate the advantages of the process according to the invention, particularly in connection with FIGS. 3 and 4. FIG. 2 shows by way of comparison a corresponding prior art distillation arrangement according to WO 2005/019160. In this prior art process, all dinitriles are withdrawn from a side draw of the corresponding distillation apparatus (D1) in liquid form. However, the process according to WO 2005/019160 does not provide for separating off the gaseous stream comprising ADN.

It is further preferable in the context of the present invention to subject the crude ADN present in stream (S1) to an additional purification, even before entry into the rectification apparatus (R1), to separate off in particular high boilers, preferably non-volatile high boilers, from the crude ADN employed. In this connection, it is also possible to return streams such as the high boiler-containing stream and the ADN-containing stream (S4) from the process (a subsequent process step) to such a first separating-off step.

It is preferable in this connection when a stream (S8) comprising crude ADN and high boilers (HB) is introduced into an evaporation apparatus (E3), wherein a stream (S1') depleted in non-volatile high boilers (HB) compared to stream (S8) is discharged from (E3) and passed into rectification apparatus (R1), and wherein a stream (S9) which comprises non-volatile high boilers and is depleted in ADN compared to stream (S8) is discharged from (E3).

Examples of useful evaporation apparatuses (E3) include single stage evaporators such as falling film evaporators, thin film evaporators, flash evaporators, multiphase helical tube evaporators, natural circulation evaporators or forced circulation flash evaporators.

It is further preferable when stream (S9) is discharged from the bottom of evaporation apparatus (E3) and passed into an evaporation apparatus (E4), wherein a stream (S10) depleted in non-volatile high boilers compared to stream (S9) is discharged from (E4) and passed into rectification apparatus (R1) and/or returned to evaporation apparatus (E3), and wherein a stream (S11) depleted in ADN compared to stream (S9) is discharged from (E4).

It is likewise preferable when some or all of stream (S4) is passed from rectification apparatus (R1) into evaporation apparatus (E3) and/or into evaporation apparatus (E4).

Figure 5:
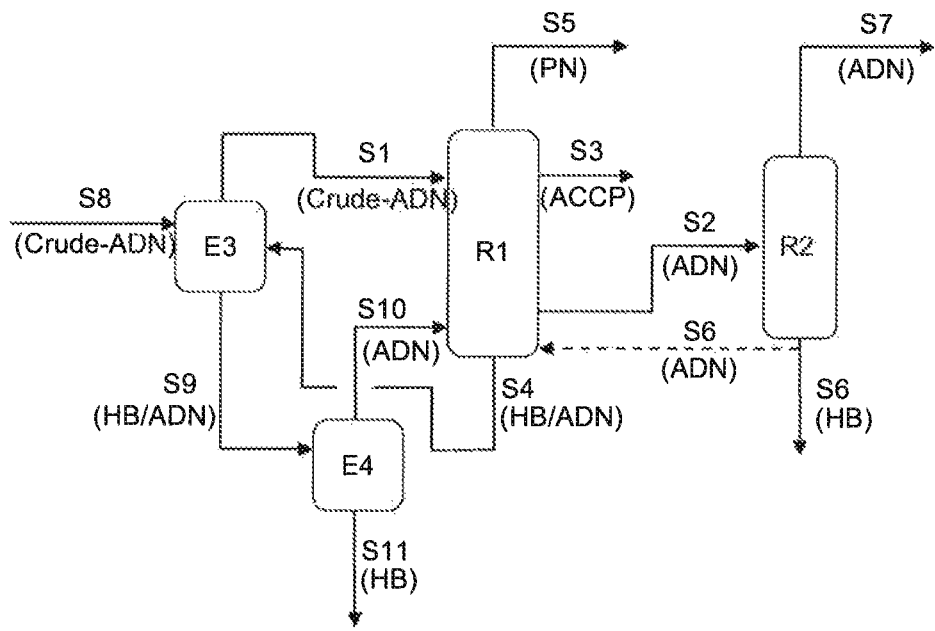
Figure 6:
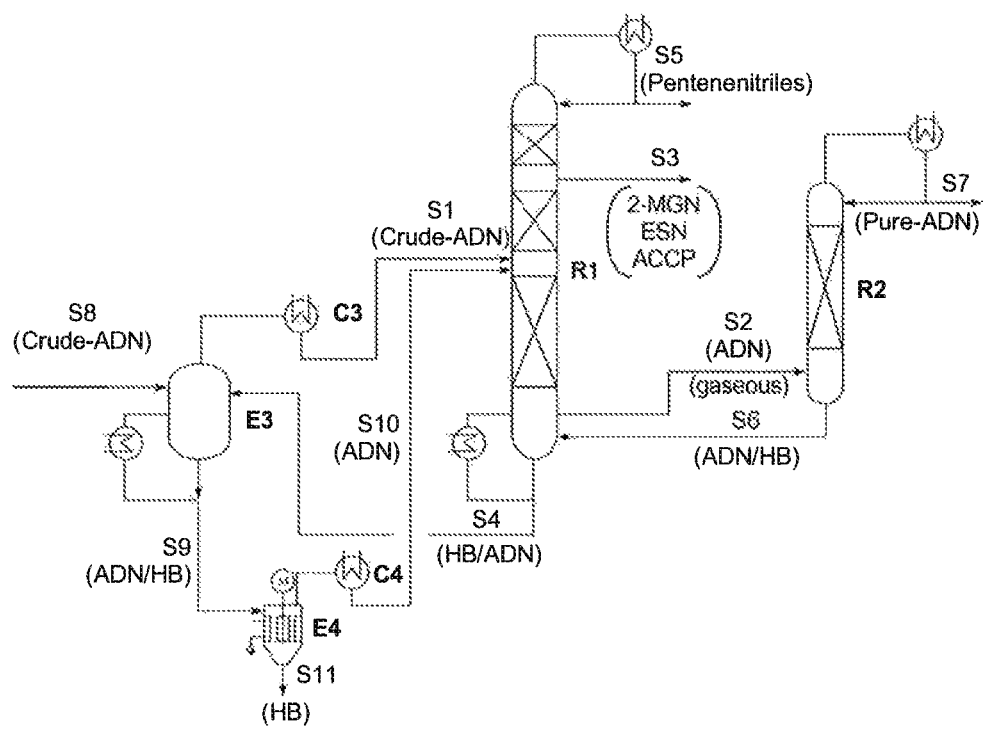

The embodiments of the present invention described hereinabove are illustrated in FIGS. 5 and 6 in terms of a preliminary separating-off of high boilers, preferably non-volatile high boilers, from the crude ADN before introduction into rectification apparatus (R1). FIG. 5 is a simplified diagram of the process while FIG. 6 shows further preferred elaborations such as condensers, apparatus internals or return lines to rectification apparatuses (R1) and (R2).

In a further preferred version of the process, shown in FIG. 6, a crude ADN stream (S8) is introduced into a distillation, rectification or preferably evaporation apparatus (E3) and evaporated before being introduced as stream (S1') into rectification apparatus (R1). This stream (S1') may be introduced into (R1) in gaseous or liquid form. Eschewing the use of a condenser (C3) can reduce the heat requirements of the evaporator of (R1). Using a condenser (C3) makes it possible to establish a lower pressure in evaporation apparatus (E3) than in rectification apparatus (R1). This makes it possible to reduce the ADN content in the bottoms output from (E3) by reducing the pressure.

In a further preferred version of the process, shown in FIG. 6, the bottoms output from evaporation apparatus (E3) is further concentrated in a further evaporation apparatus (E4) to separate ADN as overhead product while the bottoms are in enriched in high boilers. Devices that may be used as evaporation apparatus (E4) include devices familiar to those skilled in the art such as distillation chambers, natural circulation evaporators, forced circulation evaporators or preferably falling film evaporators, more preferably thin film evaporators. (E4) is preferably operated at a lower pressure than (E3). The overhead output from (E4) can be condensed in a condenser (C4) and returned to evaporation apparatus (E3) or passed into rectification apparatus (R1). The use of evaporation apparatuses (E3) and/or (E4) makes it possible to increase the yield of ADN and to reduce the losses thereof when discharging high boilers.

It is further preferable in the process according to the invention when the ADN present in the crude adiponitrile (crude ADN) is produced by a reaction of butadiene with hydrocyanic acid (HCN), wherein the ADN production process preferably comprises a first step of reacting butadiene with HCN in the presence of a nickel(0) phosphorus ligand catalyst complex (Ni—P cat) to afford 3-pentenenitrile (3-PN) and a second step of subsequently reacting 3-PN with HCN in the presence of the same Ni—P cat and a Lewis acid to afford ADN.

Alternatively, it is also possible, as described in WO 2005/073167, to use the same nickel(0) phosphorus ligand complex for the first and second hydrocyanation and the isomerization of 2-methyl-3-butenenitrile to afford 3-pentenenitriles. Nevertheless, a preferred embodiment employs the same nickel(0) complex based on a monodentate phosphorus ligand for the first hydrocyanation and the 2-methyl-3-butenenitrile isomerization and a nickel(0) phosphorus ligand complex based on a bidentate phosphorus ligand for the second hydrocyanation.

It is further preferable in the process according to the invention when the purified ADN is hydrogenated to afford hexamethylenediamine (HMD) in the presence of a hydrogenation catalyst, preferably in the presence of a Raney nickel catalyst.

The invention claimed is:

1. A process for purifying adiponitrile (ADN), comprising:
   a) introducing a stream (S1) comprising crude adiponitrile (ADN) into a rectification apparatus (R1);
   b) separating off a gaseous stream (S2) via a first side draw of (R1), wherein the first side draw of (R1) is disposed below the introduction point for introducing stream (S1) into (R1) and wherein gaseous stream (S2) comprises AND; and
   c) introducing gaseous stream (S2) into a second rectification apparatus (R2), wherein an ADN stream (S7) depleted in high boilers (HB) is drawn off from (R2) as overhead product and a liquid stream (S6) enriched in high boilers (HB) is drawn off from (R2) as bottoms.

2. The process according to claim 1, further comprising at least one of steps d), e) and f):
   d) separating off a stream (S3) via a second side draw of rectification apparatus (R1), wherein the second side draw of (R1) is disposed above the introduction point for introducing stream (S1) into (R1), and wherein stream (S3) comprises 1-amino-2-cyanocyclopentene (ACCP);
   e) separating off a stream (S5) as overhead product from rectification apparatus (R1), wherein stream (S5) comprises pentenenitriles (PNs); or
   f) separating off a stream (S4) from the bottom of rectification apparatus (R1), wherein stream (S4) comprises high boilers (HB).

3. The process according to claim 1, wherein the crude ADN in stream (S1) comprises adiponitrile (ADN), pentenenitriles (PNs), high boilers (HB), 1-amino-2-cyanocyclopentene (ACCP), 2-methylglutaronitrile (2-MGN) and 2-ethylsuccinonitrile (2-ESN).

4. The process according to claim 2, wherein:
   i) stream (S4) comprises high boilers and ADN and is liquid; or
   ii) stream (S3) comprises ACCP, 2-MGN and 2-ESN and is liquid; or
   iii) the gaseous stream (S2) comprises ADN, high boilers and no more than 500 ppm of PNs, ACCP, 2-MGN or 2-ESN.

5. The process according to claim 4, wherein in the gaseous stream (S2) the total amount of PNs, ACCP, 2-MGN and 2-ESN in (S2) is no more than 500 ppm.

6. The process according to claim 5, wherein the total amount of PNs, ACCP, 2-MGN and 2-ESN is no more than 100 ppm.

7. The process according to claim 1, wherein a stream (S8) comprising crude ADN and high boilers (HB) is introduced into an evaporation apparatus (E3), wherein a stream (S1) depleted in non-volatile high boilers (HB) compared to stream (S8) is discharged from (E3) and passed into rectification apparatus (R1), and wherein a stream (S9) which comprises non-volatile high boilers and is depleted in ADN compared to stream (S8) is discharged from (E3).

8. The process according to claim 7, wherein stream (S9) is discharged from the bottom of evaporation apparatus (E3) and passed into an evaporation apparatus (E4), wherein a stream (S10) depleted in non-volatile high boilers compared to stream (S9) is discharged from (E4) and passed into rectification apparatus (R1) or returned to evaporation apparatus (E3), and wherein a stream (S11) depleted in ADN compared to stream (S9) is discharged from (E4).

9. The process according to claim 2, wherein some or all of stream (S4) is passed from rectification apparatus (R1) into evaporation apparatus (E3) or into evaporation apparatus (E4).

10. The process according to claim 1, wherein gaseous stream (S2) is introduced into the bottom of (R2) and pure ADN is drawn off from (R2) as overhead product.

11. The process according to claim 1, wherein the ADN drawn off from (R2) as overhead product has a purity of at least 99.0%.

12. The process according to claim 11, wherein the ADN drawn off from (R2) as overhead product has a purity of at least 99.8%.

13. The process according to claim 1, wherein the total amount of PNs, ACCP, 2-MGN and 2-ESN in the ADN drawn off from (D2) as overhead product is no more than 200 ppm.

14. The process according to claim 1, wherein stream (S6) comprising high boilers (HB) and ADN is drawn off from the bottom of (R2) and some or all of said stream is returned to the bottom of rectification apparatus (R1).

15. The process according to claim 1, wherein rectification apparatuses (R1) and (R2) are each independently columns with structured packing.

16. The process according to claim 1, wherein rectification apparatus (R2) does not have an evaporator.

17. The process according to claim 1, wherein the ADN present in the crude ADN is produced by a reaction of butadiene with hydrocyanic acid (HCN).

18. The process according to claim 1, wherein the ADN production process comprises a first step of reacting butadiene with HCN in the presence of a nickel(0) phosphorous ligand catalyst complex (Ni—P cat) to afford 3-pentenenitrile (3-PN) and a second step of subsequently reacting 3-PN with HCN in the presence of the same Ni-P cat and a Lewis acid to afford ADN.

19. The process according to claim 1, wherein the purified ADN is hydrogenated to afford hexamethylenediamine (HMD) in the presence of a hydrogenation catalyst.

20. The process according to claim 1, wherein the purified ADN is hydrogenated to afford hexamethylenediamine (HMD) in the presence of a Raney nickel catalyst.

\* \* \* \* \*